(12) United States Patent
Coelho et al.

(10) Patent No.: US 7,241,281 B2
(45) Date of Patent: *Jul. 10, 2007

(54) BLOOD COMPONENT SEPARATION METHOD AND APPARATUS

(75) Inventors: Philip H. Coelho, Rancho Cordova, CA (US); Eric Sommer, Rancho Cordova, CA (US); Richard Klosinski, Carmichael, CA (US); Jim Hobbs, Carmichael, CA (US)

(73) Assignee: ThermoGenesis Corporation, Rancho Cordova, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/118,291

(22) Filed: Apr. 8, 2002

(65) Prior Publication Data

US 2003/0191005 A1    Oct. 9, 2003

(51) Int. Cl.
*A61B 19/00*   (2006.01)
*B04B 3/00*    (2006.01)
*B01D 21/26*   (2006.01)
*B01D 29/11*   (2006.01)
*B04B 1/00*    (2006.01)

(52) U.S. Cl. .................. 604/410; 604/408; 210/86; 210/87; 210/97; 210/252; 210/739; 210/782; 210/789; 494/3; 494/4; 494/43; 494/45; 494/20

(58) Field of Classification Search ............. 210/739, 210/782, 787, 789, 95, 86, 87, 94, 97, 109, 210/112, 252, 257.1, 85; 494/1, 2, 3, 5, 10, 494/19, 20, 37, 43, 45; 604/408, 410
See application file for complete search history.

(56) References Cited

U.S. PATENT DOCUMENTS

| 3,987,961 | A | * | 10/1976 | Sinn et al. ................... 494/45 |
| 4,608,178 | A | * | 8/1986 | Johansson et al. .......... 210/744 |
| 4,720,284 | A | * | 1/1988 | McCarty ...................... 494/37 |
| 4,844,810 | A | * | 7/1989 | Richalley et al. ........... 210/646 |
| 4,946,434 | A | * | 8/1990 | Plaisted et al. .............. 494/29 |
| D314,824 | S | | 2/1991 | Moon |
| 5,102,407 | A | * | 4/1992 | Carmen et al. ............. 604/410 |
| 5,330,462 | A | * | 7/1994 | Nakamura .................. 604/410 |
| 5,674,173 | A | | 10/1997 | Hlavinka et al. |
| 5,723,050 | A | * | 3/1998 | Unger et al. ................ 210/772 |
| 5,769,839 | A | * | 6/1998 | Carmen et al. ............. 604/408 |
| 5,792,038 | A | | 8/1998 | Halvinka |
| 5,836,934 | A | * | 11/1998 | Beshel ....................... 604/410 |
| 5,921,950 | A | | 7/1999 | Toavs et al. |
| 6,251,284 | B1 | * | 6/2001 | Bischof et al. ............. 210/739 |

(Continued)

FOREIGN PATENT DOCUMENTS

WO    WO 95/01842    1/1995

*Primary Examiner*—Krishnan S. Menon
(74) *Attorney, Agent, or Firm*—Bernhard Kreten; Audrey A. Millemann; Weintraub Genshlea Chediak

(57) ABSTRACT

An apparatus and method for collecting whole blood and then separating it into components for subsequent use or storage. A self-contained bag set is used to collect the sample, which may then be placed into container adapted to fit into a centrifuge for separation of components. Each component is then sequentially extracted according to density, with a sensor present in the container to control the operation of valves directing the collection of each component. Each component may then be separated into its own storage container.

5 Claims, 7 Drawing Sheets

U.S. PATENT DOCUMENTS 6,315,706 B1    11/2001   Unger et al.
6,322,709 B1 * 11/2001   Krasnoff et al. ............ 210/739
6,348,031 B1     2/2002   Unger et al.
6,495,039 B1 * 12/2002   Lee et al. ................ 210/257.1
6,652,475 B1 * 11/2003   Sahines et al. ............ 604/6.01

* cited by examiner

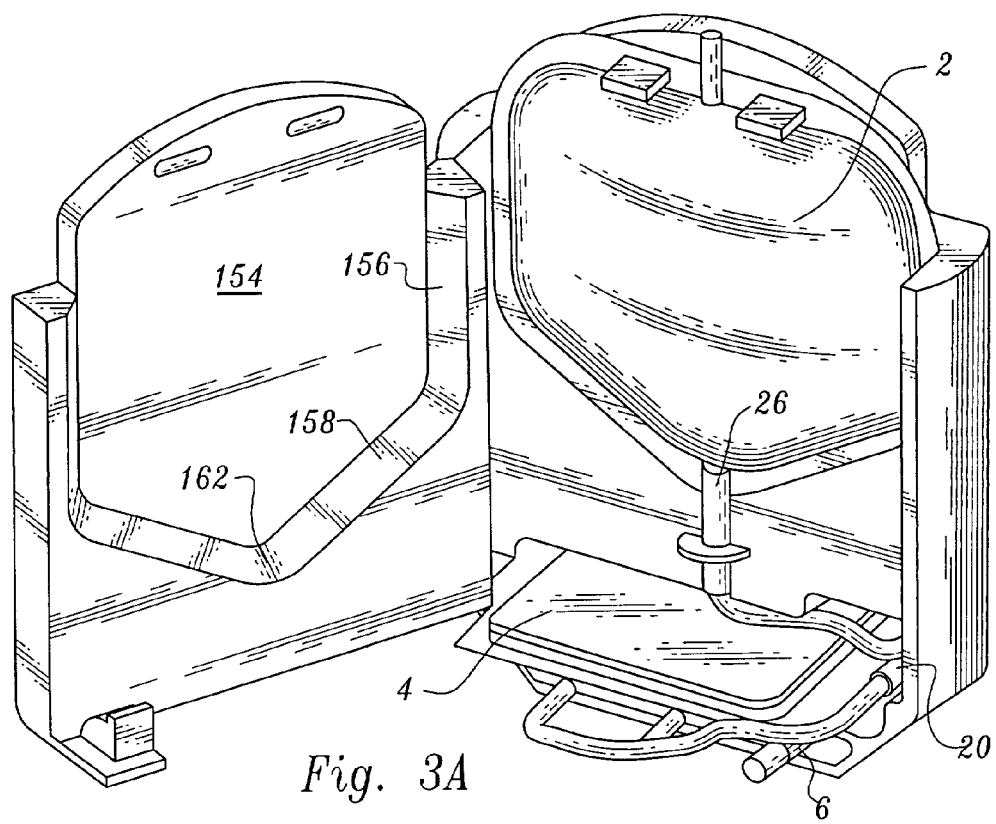
Fig. 3A
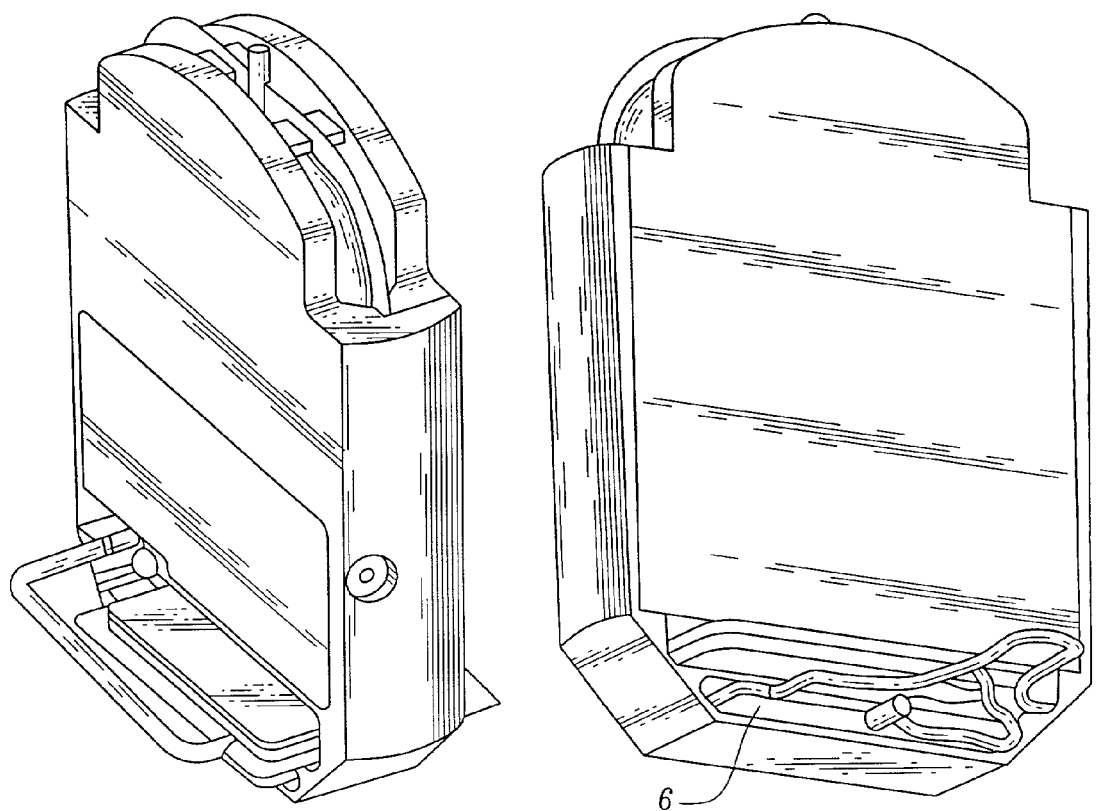
Fig. 3B                                    Fig. 3C

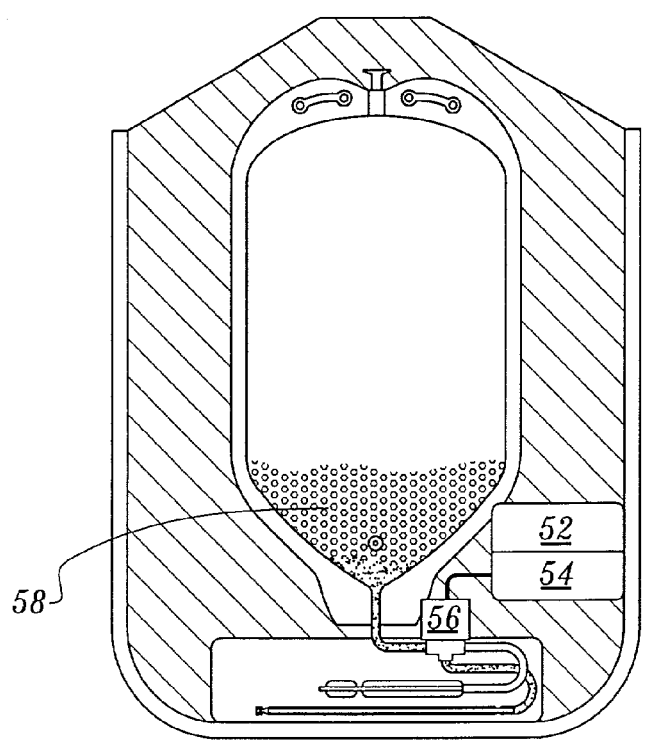
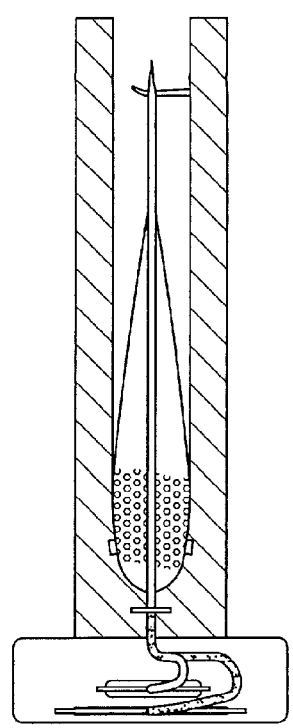
Fig. 6A                Fig. 6B
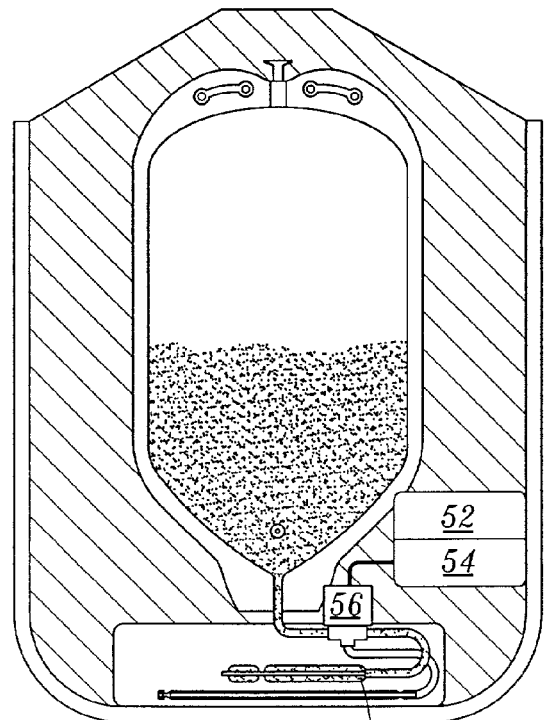
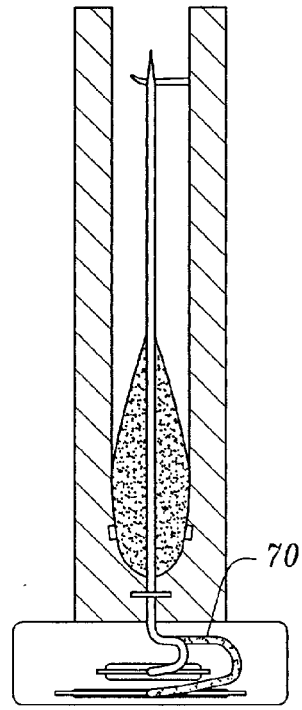
Fig. 7A                Fig. 7B

BLOOD COMPONENT SEPARATION METHOD AND APPARATUS

FIELD OF THE INVENTION

The following invention relates generally to instrumentalities and methodologies in blood component separation techniques. More specifically, the instant invention is directed to a method and apparatus for collecting a blood sample and subsequently separating the collected sample into the blood components for individual storage or use.

BACKGROUND OF THE INVENTION

Blood collection is always important, particularly in times of emergency (immediate use), but whole blood may only be stored for about 30 days before it is "outdated". For long term storage, the ability to separate the whole blood into its major components (white blood cells, platelets, red blood cells and plasma) is of paramount importance because the long term storage conditions for each component is different in terms of temperature and storage media. The most important component separations occurring after collection is the separation of red blood cells (RBC), white blood cells (WBC), platelets, and plasma from one another. Within the WBC it is sometimes important to separate the granulocytes from the lymphocytes. After separation and extraction of particular components, a fraction of the blood may be returned to the patient.

It is possible to separate the various components of whole blood either under or after centrifugation, due to their differing densities. Some prior art methods, such as that in U.S. Pat. No. 4,120,448, utilize a chamber connected to a centrifuge. The centrifuged blood separates in the chamber, and a plurality of collection means are positioned at various locations in the chamber corresponding to the areas where each component congregates, which is density-dependent.

SUMMARY OF THE INVENTION

The present invention comprises a bag set that may be used to collect a whole blood sample from a source, then placed into a centrifuge for component separation. The whole blood collection bag, which contains an anticoagulant such as CPD, ACD or CPD-A, contains one outlet port connected to a plurality of component collection bags. Each component collection bag has a separate line leading from the whole blood collection bag, and each line can be clamped, tube-sealed and separated from the whole blood collection bag once a particular component bag has been filled.

In practice, the blood is collected into the whole blood collection bag and the input line is clamped, sealed off, and separated from the whole blood collection bag. The whole blood collection bag hangs in a clamshell-style container that closely contacts the bag at the bottom end, and is adapted to fit in a centrifuge cup. The centrifuge is operated at varying G-forces to optimally separate the components. Once the components are separated in the whole blood collection bag, a driver motor is engaged to open a metering valve on the line leading from the collection bag to a bag that will contain the densest component. This allows the densest component to fill its particular storage bag.

Complete collection of the first component is indicated by an optical sensor that is present in the clamshell container. The driver motor, directed by the sensor, automatically closes the metering valve on the line, terminating collection of that particular component. The driver motor then further engages the metering valve to allow collection of the next component through a second output line connecting the metering valve and the second storage bag. The process may sequentially continue until all desired components are collected in separate storage bags: red blood cells, white blood cells (lymphocytes and granulocytes), platelets, and plasma.

Once collected, each storage bag may be sealed off and separated from the whole blood collection bag. Any necessary preservatives or additives may be introduced through the collection lines before processing or storing.

OBJECTS OF THE INVENTION

Accordingly, it is a primary object of the present invention to provide a new and novel device and method for separating the components of whole blood for subsequent storage or use.

It is a further object of the present invention to provide a device and method as characterized above in which separation may be accomplished entirely by machine during a single centrifugation run without the considerable handling and multiple centrifugation runs typically practiced in a blood bank.

It is a further object of the present invention to provide a device and method as characterized above in which the separation apparatus is self-contained to simplify the operation.

Viewed from a first vantage point, it is an object of the present invention to provide a bag set, comprising, in combination: a centrifuge bag leading to first and second bags; an inlet to allow blood into said centrifuge bag; conduits leading from said centrifuge bag to said red and white blood cell bags; and valve means operating under machine control to admit blood fractions to said first and second bags.

Viewed from a second vantage point, it is an object of the present invention to provide a system for separating blood cells, comprising, in combination: a centrifuge; a bag set having plural interconnected bags; and a bag set container contoured to be received in said centrifuge, said container including means to selectively provide access between bags within said bag set.

Viewed from a third vantage point, it is an object of the present invention to provide a method for separating blood cells, the steps including: centrifuging a mixture of blood cells to cause stratification, the stratification producing a first cell layer and a second cell layer; opening a conduit leading to a first cell bag; centrifuging the first cell layer into the first cell bag; closing the conduit to the first cell bag; opening a conduit leading to a second cell bag; and centrifuging the second cell layer to the second cell bag.

These and other objects will be made manifest when considering the following detailed specification when taken in conjunction with the appended drawing figures.

BRIEF DESCRIPTION OF THE DRAWINGS

FIGS. 3A–3C depict the clamshell bag holder after insertion of the bag set.

FIGS. 6A and 6B depict the harvesting of the greater-density component.

FIGS. 7A and 7B depict the harvesting of the lesser-density component.

DESCRIPTION OF PREFERRED EMBODIMENTS

Figure 1:
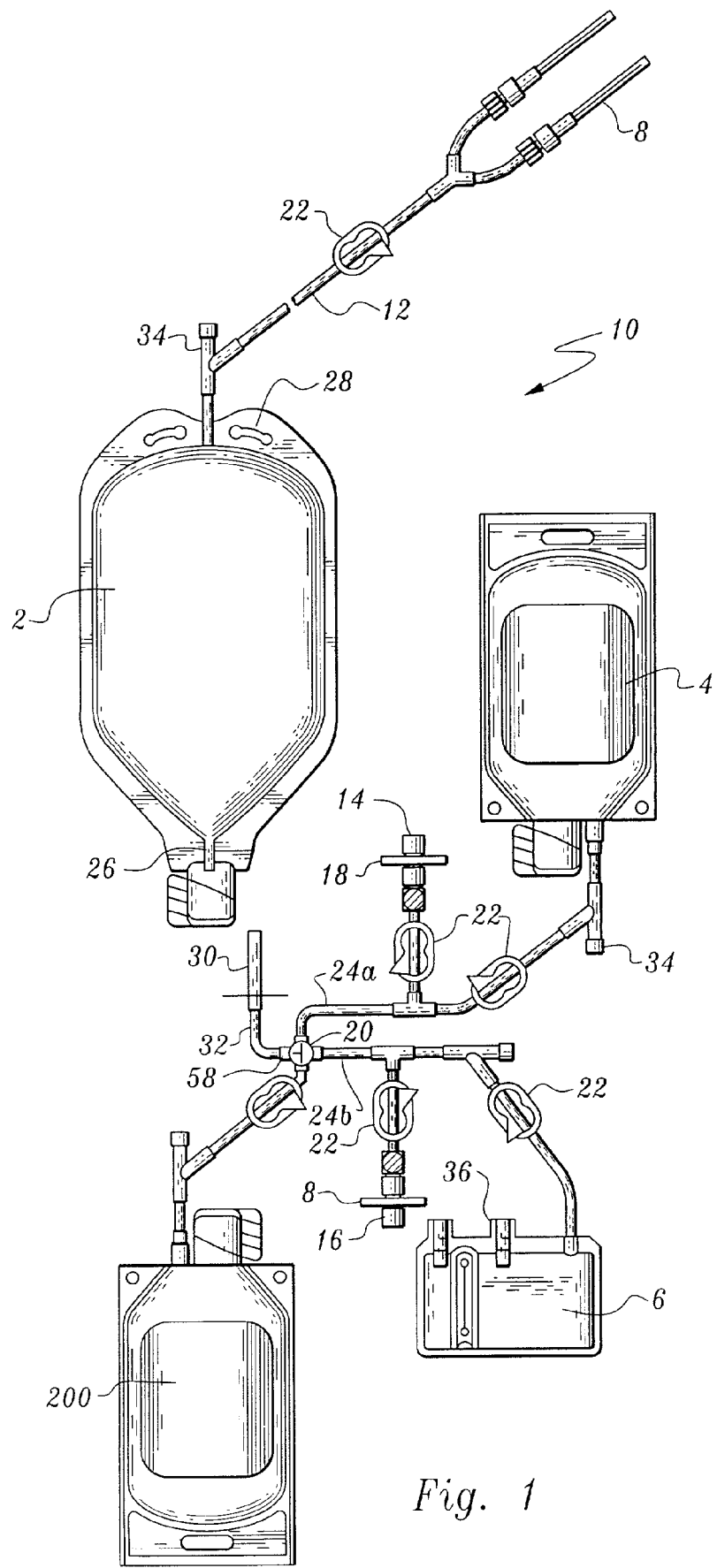
FIG. 1 depicts the bag set of the present invention.

Considering the drawings, wherein like reference numerals denote like parts throughout the various drawing figures, reference numeral 10 as shown in FIG. 1 is directed to the bag set according to the present invention.

Figure 9A:
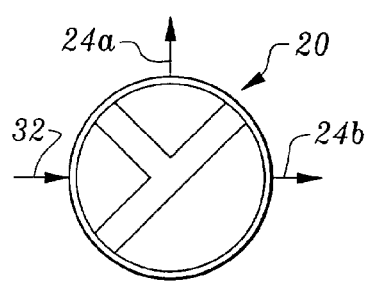
FIGS. 9A–9C depict the operating positions of the metering valve.
Figure 9B:
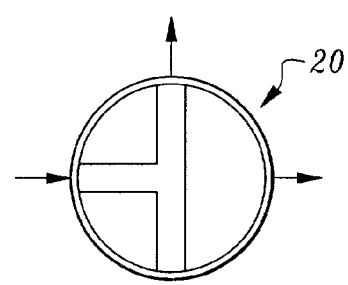
Figure 9C:
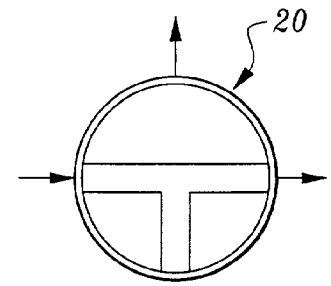
Figure 10:
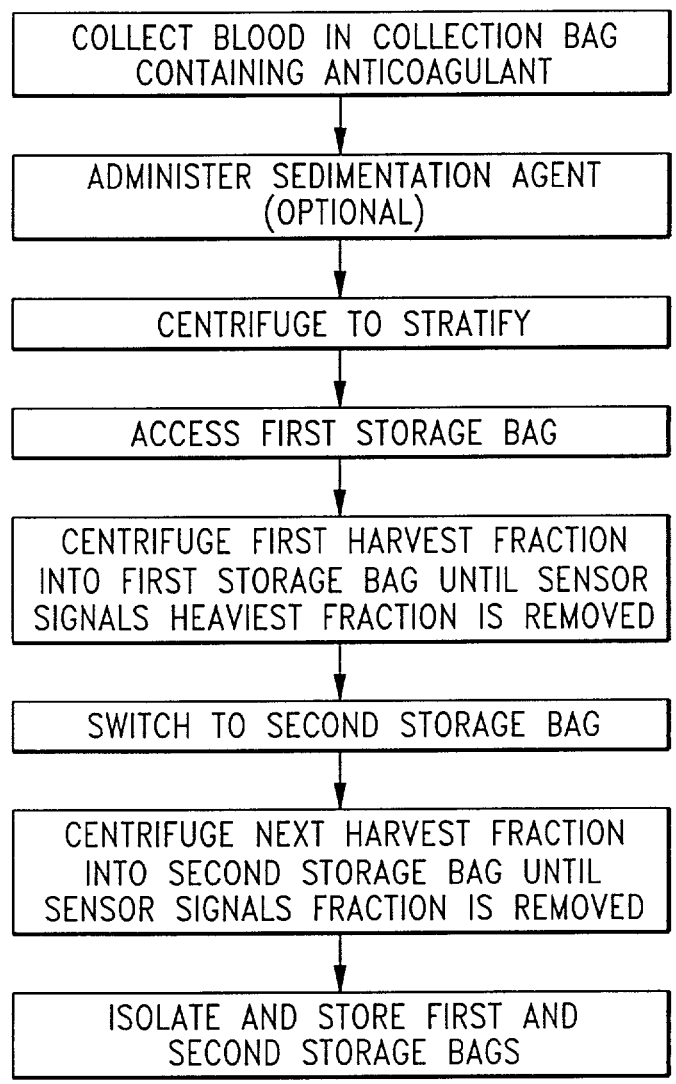
FIG. 10 is a flowchart of the preferred process.

Referring to FIG. 1, the bag set 10 includes a whole blood collection bag 2, a red blood cell (RBC) bag 4, and a freezing bag 6 for the collection and storage of white blood cells. The collection bag 2 is supplied through an inlet line 12, preferably through a phlebotomy needle 8. The collection bag 2 has an outlet 26, which directs output into a three-way metering valve 20 through a spike 30 (which is inserted into outlet 26) which is connected to an outlet line 32. The operation positions of the metering valve 20 are shown in FIGS. 9A–9C. Two supply lines 24a,24b lead from the metering valve 20 to the RBC bag 4 and the freezing bag 6, respectively. RBC supply line 24a has an optional HES inlet 14 for the introduction of a sedimenting agent, such as hydroxyethyl starch (HES) into the system. The freezing bag supply line 24b has an optional cryoprotectant inlet 16 for the introduction of cryoprotectant into the system. The HES inlet 14 and the cryoprotectant inlet 16 are each equipped with a filter 18, preferably a 0.2μ filter, to, inter alia, prevent contamination from pathogens in the outside air and to allow venting of air from the freezing bag and tubing. The supply lines 24a,24b and the inlet line 12 may each be heat sealed and separated from the bag set 10. All lines are equipped with line clamps 22 that may be closed to prevent fluid passage when desired. If other components are to be separated, the bag set 10 may include additional bags 200, and the metering valve 20 may be modified to accommodate the additional bags 200.

Initially, the collection bag 2 is filled with an anticoagulant, such as CPD (citrate, phosphate, and dextrose). The metering valve 20 begins in the closed position (FIG. 9A). All clamps 22 are closed, with the exception of the clamp 22 on the inlet line 12. Blood, preferably whole, placental, or umbilical cord blood, is obtained from a source through the phlebotomy needle 8 or other appropriate inlet, which feeds into the collection bag 2 through the inlet line 12. The inlet line 12 is then clamped, heat sealed, and separated from the bag set 10. The clamps 22 on the HES inlet line 14 are opened, and HES is introduced through the HES inlet 14 into bag 2. The line leading to the HES inlet 14 is then clamped, heat sealed, and removed. Alternatively, the HES can be introduced into the bag 2 earlier, as, for example, during manufacture.

Figure 2A:
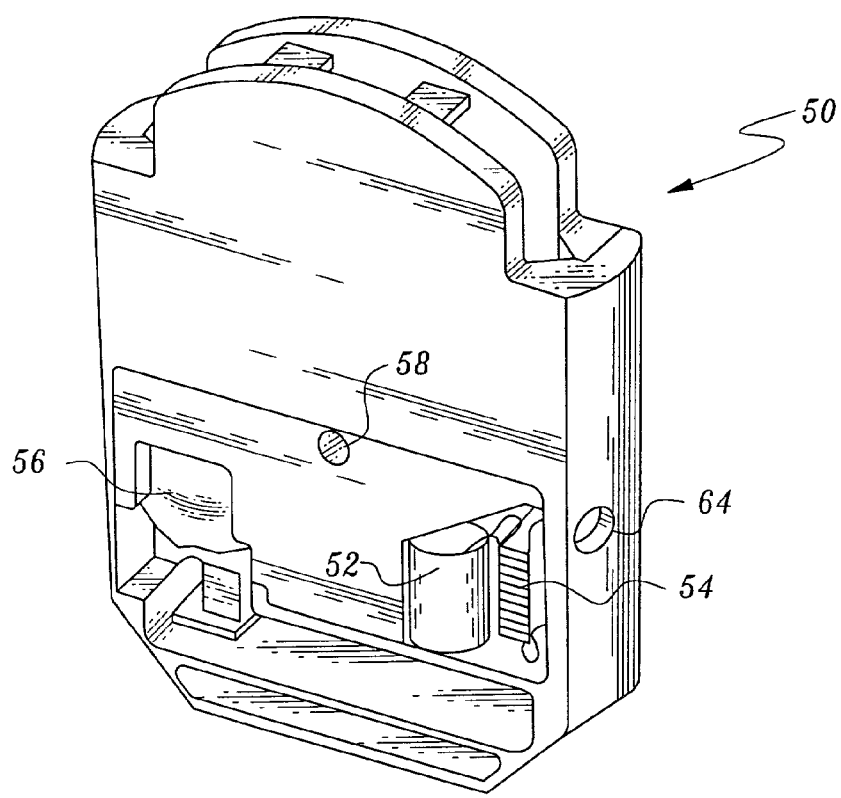
FIGS. 2A and 2B depict the clamshell container before insertion of the bag set.
Figure 2B:
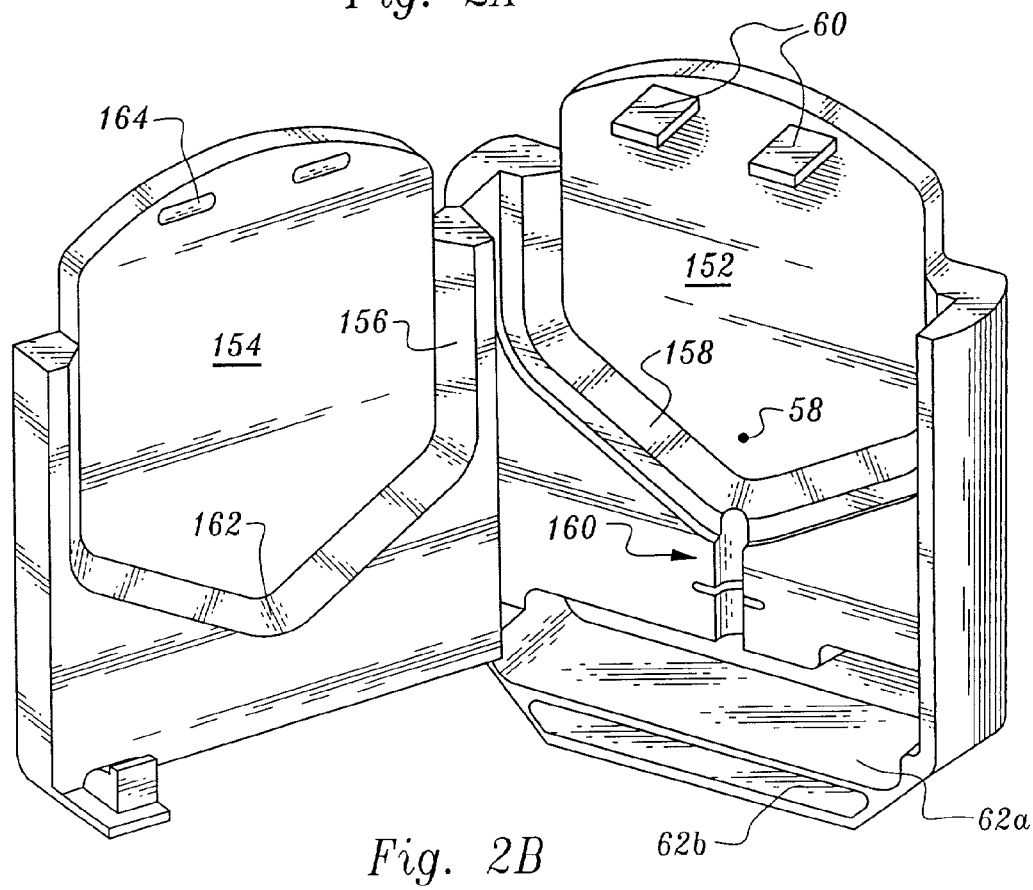
Figure 4A:
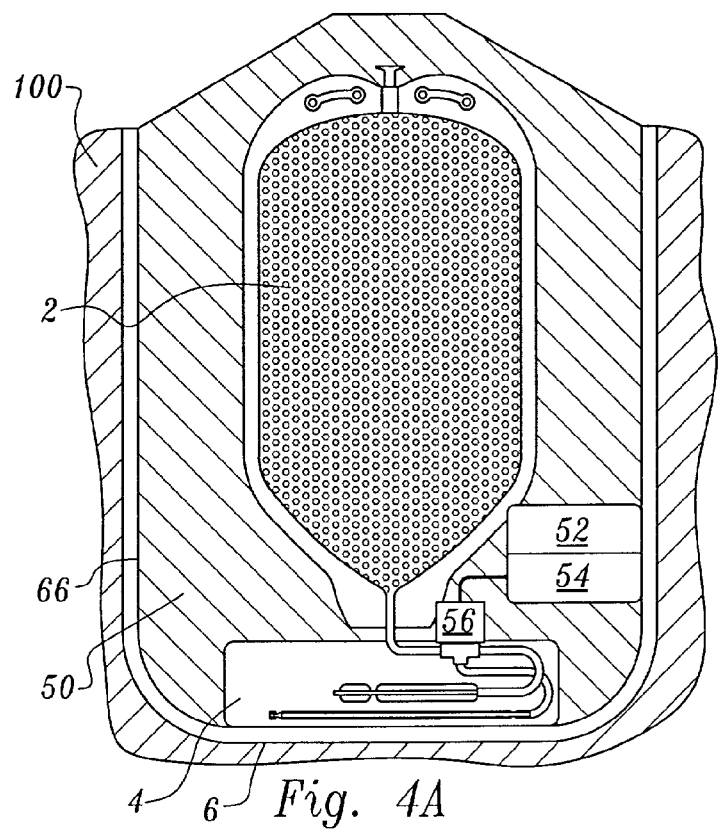
FIGS. 4A and 4B depict the bag set in the chamber before centrifugation.
Figure 4B:
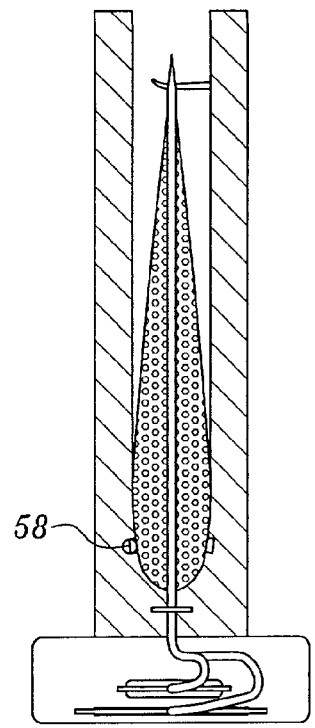

At this point, the bag set 10 is placed in a clamshell bag holder 50, shown in FIGS. 3A–3C. Referring to FIGS. 2A, 2B, the bag holder 50 includes hooks 60 that engage the loops 28 on the collection bag 2. The interior of the bag holder 50 is shaped to receive the collection bag 2, having a bag holding wall 152, a bag-supporting wall 154, and straight sidewalls 156 near the top of the bag holder 50, which intersect with angled walls 156 at the bottom of the collection bag 2. The angled walls 156 terminate at the bottom of the bag-holding wall 152 in an outport 160 dimensioned to receive the outlet 26 of the collection bag 2. On the bag-supporting wall 154, the angled walls 158 terminate at an angled point 162. The sidewalls 156,158 help to cradle the collection bag 2 loosely at the top (near the loops 28) and more tightly at the bottom (near the outlet 26). Closer tolerance near the bottom of bag 2 is desired to minimize disturbing the contents of the bag after sedimentation. The metering valve 20 is connected to a motor driver 56 in the bag holder 50. The motor driver 56 is connected to a software-controlled wireless control chip module 54 powered by a rechargeable battery 52. A port 64 is provided to utilize a battery charger. The motor driver 56 controls the operation of the metering valve 20 while the bag set 10 is mounted in the bag holder 50. One or more optical sensors 58 (e.g., FIGS. 2A, 2B) positioned near the collection bag outlet 26 and/or located on the bag holder 50 triggers the proper time for the motor driver 56 to close the metering valve 20 after each fraction is harvested. Alternatively, an optical sensor 58 (FIG. 1) may be located just upstream of the metering valve 20 to allow greater control over the harvest of each component by "reading" strata change closest to the metering valve 20. The bag holder 50, when closed, is adapted to fit into a centrifuge cup 66 dimensioned to reside within a conventional centrifuge 100 (FIG. 4A). The RBC bag 4 and the freezing bag 6 are cradled in the bottom of the bag holder 50 in separate recesses 62a,62b (FIGS. 2A, 2B) of the bag holder 50.

Figure 5A:
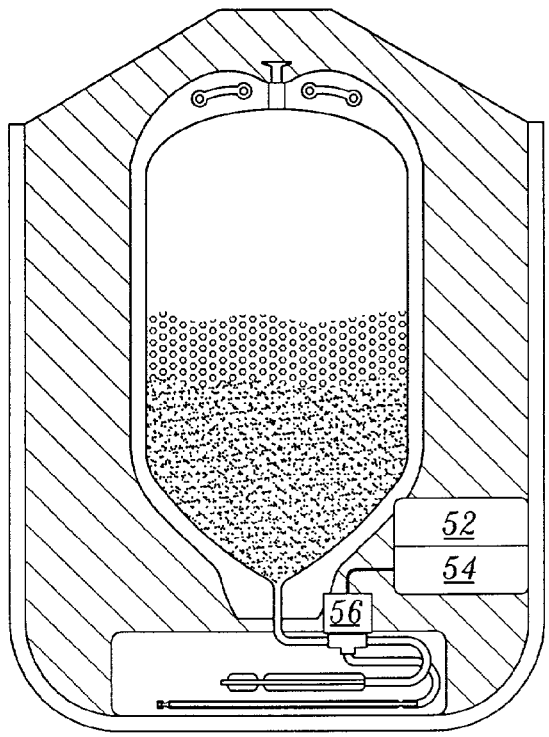
FIGS. 5A and 5B depict the bag set in the chamber after centrifugation.
Figure 5B:
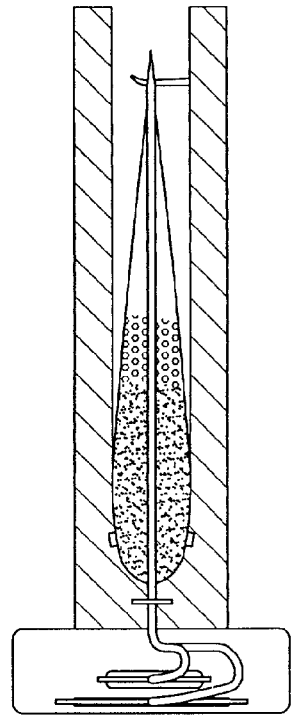

The bag set 10 in the centrifuge cup 66 may be subjected to more than one G-force in order to achieve the optimum stratification of components (FIGS. 5A, 5B). The motor driver 56 then operates the metering valve 20 to open and allow access to supply line 24a for the harvest of red blood cells, at an optimum G-force, into bag 4. The motor driver 56 closes the metering valve 20 when the optical sensor 58 indicates that the red blood cells are harvested (FIGS. 6A, 6B). The next fraction, which includes white cells and/or platelets, is then harvested from the collection bag 2; the motor driver 56 opens the metering valve 20 to allow access to supply line 24b (FIG. 9C) leading to bag 6 for the next harvest. As shown in FIGS. 7A, 7B, during the harvest (WBC) into the freezing bag 6, air in the supply line adds to air already in the freezing bag 6, producing an air bubble 70, which is useful to assist the proper mixing of the WBC and/or platelets with the cryoprotectant. The motor driver 56 then closes the metering valve 20, as shown in FIG. 9A, and the centrifuge 100 is allowed to stop.

Figure 8A:
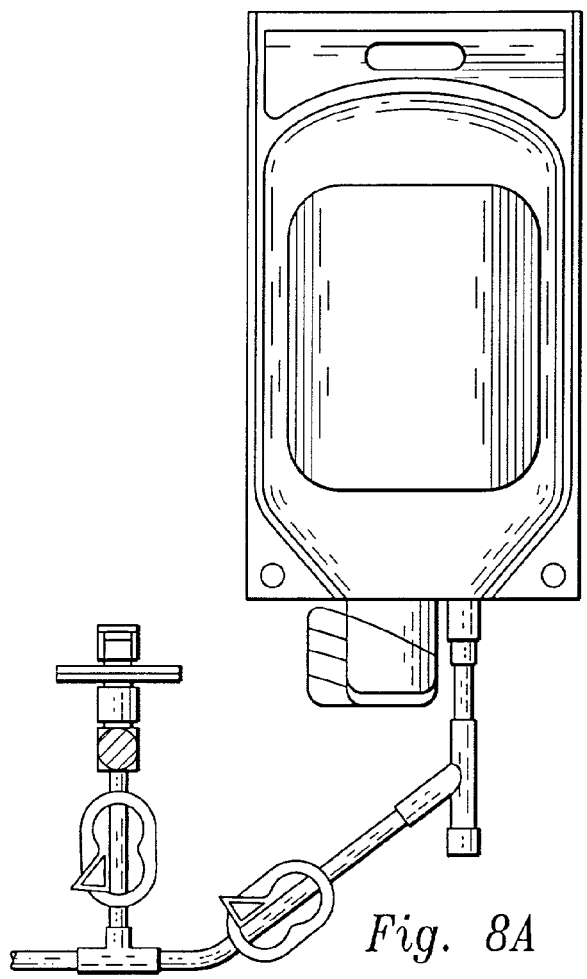
FIGS. 8A and 8B depict the separate collection lines of the bag set after disconnection from the collection bag.
Figure 8B:
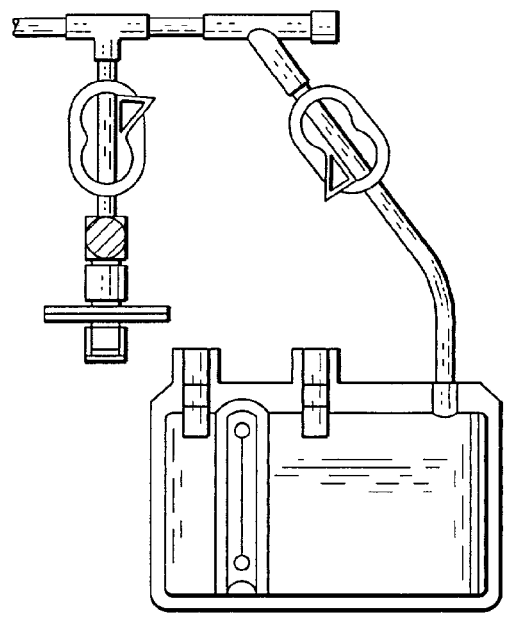

The bag holder 50 is removed from the centrifuge cup 66 and opened, and the bag set 10 is removed, with the motor driver disconnected from the metering valve 20. Each supply line 24a,24b is clamped, heat sealed, and removed from the collection bag 2 (FIGS. 8A, 8B). Any additional bags 200 (FIG. 1) may be similarly removed.

After the supply line 24b connected to the freezing bag 6 is disconnected, a cryoprotectant may be introduced into the component in the freezing bag 6 through cryoprotectant inlet 16. The air bubble 70 in the freezing bag 6 allows the cryoprotectant to be thoroughly mixed with the collected component. After mixing, the air bubble 70 is expelled through the filter 18 of the cryoprotectant inlet 16. The component is then prepared for storage by heat-sealing the tubing and removing the bag 6 downstream of the cryoprotectant inlet 16.

Preferably, each line (the inlet line 12 and the supply lines 24a,24b) is oriented to allow access to a sampling site 34 near the collection or storage bags. Thus, a sample of the blood or fluid in the line may be taken without disturbing the bulk of the collected component.

Figure 11:
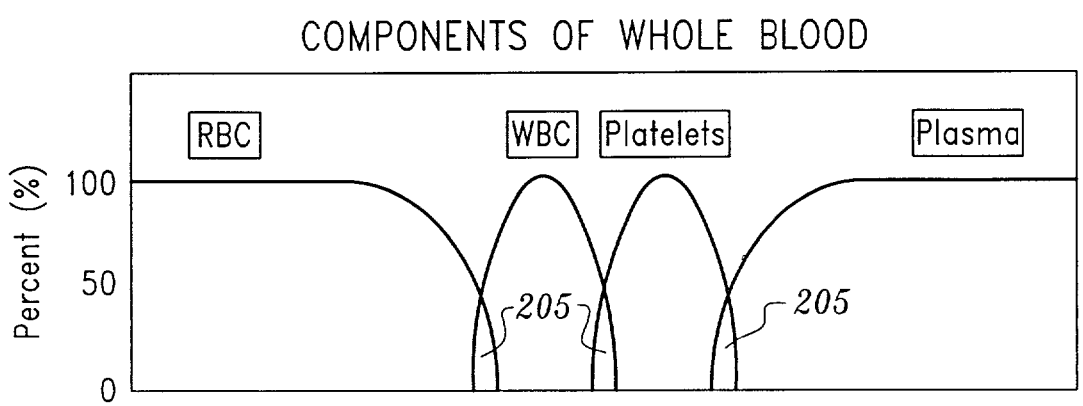
FIG. 11 illustrates the separation of whole blood components in graphical form.

FIG. 11 depicts the separation of whole blood components as a function of time. Under centrifugation, each fraction stratifies in the collection bag 2 as a function of its density. The overlapping areas 205 indicate the area in the separation along each strata line in the collection bag 2. As centrifugation continues, the boundary of each fraction becomes more clearly defined; thus, the area 205 decreases and each fraction is more completely harvested. Thus, the centrifugation strategy combines separation by density, the time involved for stratification, centrifuge force, and boundary layer clarity. Decisions on harvesting will vary based on these tradeoffs as a function of the constituent of greatest value and its desired purity.

It is appreciated that while the instant invention is preferably used in the separation of blood components, the separation techniques and apparatus are suitable for separation of other fluids. The software programmed into the control chip module may cause the motor driver to open and close the valve many times, thereby throttling the valve during strata delivery. Also by varying time increments during a harvest procedure, precise cut-offs between the cell components can be achieved in order to reduce the mixing between cell types that may occur as a result of the "toroidal" (Coriolis) effect during removal of the blood component from bag 2 and may be modified for the separation of other fluids or to compensate for various hardware conditions, such as uneven centrifuge loading. Moreover, having thus described the invention, it should be apparent that numerous structural modifications and adaptations may be resorted to without departing from the scope and fair meaning of the instant invention as set forth hereinabove and as described hereinbelow by the claims.

We claim:

1. A bag set for use in a conventional centrifuge characterized by a plurality of cups radially disposed about a non-bag-supporting center, comprising, in combination:
   a centrifuge bag having a distinct inlet for receiving blood and a distinct outlet leading to the first and second bags, all said bags disposed in one cup, whereby said inlet and said outlet are located at opposite ends of said centrifuge bag;
   supply lines leading from said centrifuge bag to said first and second bags;
   a three-way metering valve operatively interposed between said outlet and said supply lines, said valve controlled by a motor during a centrifugation cycle to admit blood fractions to said first and second bags, whereby red blood cells are admitted to said first bag while under centrifugation and white blood cells are admitted to said second bag also while under centrifugation, producing a red blood cell bag and a white blood cell bag;
   a holder for said bag set which ensconces said centrifuge bag and said red and white blood cell bags, said valve in said bag set and communicating with said holder and operatively coupled to said motor located on said holder, said holder adapted to fit into one cup of the conventional centrifuge; and
   a sensor in said holder, said sensor monitoring a transition from red to white blood cells, whereupon said valve diverts flow of blood cells from said red blood cell bag to said white blood cell bag via said motor.

2. A method of separating blood cells using a conventional centrifuge, the steps including:
   collecting a mixture of blood cells in a centrifuge bag by introducing the blood cells therewithin via a distinct inlet line feeding said centrifuge bag,
      wherein said centrifuge bag has a distinct outlet leading to a first and a second bag, all said bags defining a bag set, whereby said inlet and said outlet are located at opposite ends of said centrifuge bag;
      wherein supply lines lead from said centrifuge bag to said first and second bags;
      wherein said bag set further includes a three-way metering valve operatively interposed between said outlet and said supply lines, said valve controlled by a motor during a centrifugation cycle to admit blood fractions to said first and second bags;
   ensconcing said bag set in a bag set holder, said valve in said bag set and communicating with said holder and operatively coupled to said motor located on said holder, said bag set holder adapted to fit into one of plural cups of the conventional centrifuge, said bag set holder further including a sensor, said sensor monitoring a transition from red to white blood cells;
   centrifuging said mixture of blood cells to cause stratification, the stratification producing a red blood cell layer and a white blood cell layer;
   opening said valve on said outlet extending from said centrifuge bag to allow access to said supply line leading to said first bag;
   centrifuging said red blood cell layer into said first bag;
   closing said valve;
   opening said valve to allow access to said supply line leading to said second bag; and
   centrifuging said white blood cell layer into said second bag.

3. A method of separating blood components in a conventional centrifuge using the bag set of claim 1, the steps including:
   collecting a mixture of blood cells into said centrifuge bag;
   ensconcing said centrifuge bag and said first and second bags in said holder;
   loading said holder and said bag set in a cup of the centrifuge, centrifuging said mixture of blood cells to cause stratification, said stratification producing a plurality of cell layers;
   activating said sensor in said holder to sense boundaries of said cell layers; and
   centrifuging each of said cell layers into a separate one of said first and second bags.

4. The bag set of claim 1, wherein said valve opens sequentially to allow each of said blood fractions through said supply lines into said first and second bags, and closes sequentially after each of said blood fractions is admitted to each of said first and second bags.

5. The bag set of claim 1, wherein said valve, in sequence, opens to admit the red blood cells into said first bag, closes after the red blood cells have been admitted into said first bag, opens to admit the white blood cells into said second bag, and closes after the white blood cells have been admitted into said second bag.

* * * * *